(12) United States Patent
Jessen et al.

(10) Patent No.: US 6,316,489 B1
(45) Date of Patent: Nov. 13, 2001

(54) SALT OF (2R,3R,4R)-3,4-DIHYDROXY-2-HYDROXYMETHYLPYRROLIDINE

(75) Inventors: Claus Ulrich Jessen, Vanlose (DK); Petra Christine Lugstein, Wien (AT)

(73) Assignee: Novo Nordisk A/S, Bagsvaerd (DK)

( * ) Notice: Subject to any disclaimer, the term of this patent is extended or adjusted under 35 U.S.C. 154(b) by 0 days.

(21) Appl. No.: 09/523,012

(22) Filed: Mar. 10, 2000

Related U.S. Application Data

(60) Provisional application No. 60/125,268, filed on Mar. 19, 1999.

(30) Foreign Application Priority Data

Mar. 15, 1999 (DK) .............................................. 1999 00363

(51) Int. Cl.[7] .................................................... A61K 31/40
(52) U.S. Cl. ............................................................... 514/425
(58) Field of Search ............................................. 514/425

(56) References Cited

FOREIGN PATENT DOCUMENTS

| | | |
|---|---|---|
| 42 02 183 A1 | 7/1993 | (DE) . |
| 42 02 184 A1 | 7/1993 | (DE) . |
| 0 846 464 A2 | 6/1998 | (EP) . |
| WO 95/24391 | 9/1995 | (WO) . |
| WO 96/39384 | 12/1996 | (WO) . |
| WO 96/39385 | 12/1996 | (WO) . |
| WO 97/09040 A1 * | 3/1997 | (WO) . |
| WO 98/40353 A1 * | 9/1998 | (WO) . |
| WO 98/50359 | 11/1998 | (WO) . |

OTHER PUBLICATIONS

Windholz, M., Editor–in–Chief of The Merck Index, Tenth Edition, No. 8945, p. 1303, Jun. 21, 1983.*
Ralph A. DeFronzo, Diabetes, vol. 37, pp. 667–687 (1988).
Abstract of Japanese Patent JP–255184 A2.

* cited by examiner

Primary Examiner—Dwayne C. Jones
(74) Attorney, Agent, or Firm—Reza Green, Esq.; Valeta A. Gregg, Esq.

(57) ABSTRACT

This invention relates to (2R,3R,4R)-3,4-dihydroxy-2-hydroxymethylpyrrolidine D-tartrate, preparation thereof and use as therapeutic agent.

9 Claims, No Drawings

SALT OF (2R,3R,4R)-3,4-DIHYDROXY-2-HYDROXYMETHYLPYRROLIDINE

CROSS-REFERENCE TO RELATED APPLICATIONS

This application claims priority under 35 U.S.C. 119 of Danish application PA 1999 00363 filed on Mar. 15, 1999, and U.S. application No. 60/125,268 filed on Mar. 19, 1999, the contents of which are fully incorporated herein by reference.

FIELD OF THE INVENTION

This invention relates to (2R,3R,4R)-3,4-dihydroxy-2-hydroxymethylpyrrolidine D-tartrate, its preparation and use as therapeutic agent.

BACKGROUND OF THE INVENTION

Diabetes

Diabetes is characterised by an impaired glucose metabolism manifesting itself among other things by an elevated blood glucose level in the diabetic patients. Underlying defects lead to a classification of diabetes into two major groups: type 1 diabetes, or insulin demanding diabetes mellitus (IDDM), which arises when patients lack β-cells producing insulin in their pancreatic glands, and type 2 diabetes, or non-insulin dependent diabetes mellitus (NIDDM), which occurs in patients with an impaired β-cell function besides a range of other abnormalities.

Type 1 diabetic patients are currently treated with insulin, while the majority of type 2 diabetic patients are treated either with sulfonylureas that stimulate β-cell function or with agents that enhance the tissue sensitivity of the patients towards insulin or with insulin. Among the agents applied to enhance tissue sensitivity towards insulin metformin is a representative example.

In normal as well as in diabetics, the liver produces glucose in order to avoid hypoglycaemia. This glucose production is derived either from the release of glucose from glycogen stores or from gluconeogenesis, which is a de novo intracellular synthesis of glucose. In type 2 diabetes, however, the regulation of hepatic glucose output is poorly controlled and is increased, and may be doubled after an overnight fast. Moreover, in these patients there exists a strong correlation between the increased fasting plasma glucose levels and the rate of hepatic glucose production (reviewed in R. A. De Fronzo: *Diabetes* 37 (1988), 667–687; A. Consoli: *Diabetes Care* 15 (1992), 430–441; and J. E. Gerich:*Horm.Metab.Res.* 26 (1992), 18 –21). Similarly, hepatic glucose production will be increased in type 1 diabetes, if the disease is not properly controlled by insulin treatment.

Since the liver in diabetes is known to have an increased glucose production, compounds inhibiting this activity are highly desirable. Recently, patent applications on inhibitors of the liver specific enzyme, glucose-6-phosphatase, which is necessary for the release of glucose from the liver, have been filed, for example German Offenlegunqsschrift Nos. 4,202,183 and 4,202,184 and Japanese patent application No. 4-58565. All these known compounds are benzene derivatives.

Glycogen phosphorylase is another enzyme, which is necessary for the release of glucose from the liver. Substituted N-(indole-2-carbonyl)-glycinamides acting as glycogen phosphorylase inhibitors are disclosed in PCT-publications No. WO96/39384 and WO96/39385 and in EP-A-0 846 464. Piperidine and pyrrolidine compounds acting as glycogen phosphorylase inhibitor are disclosed in PCT-publication No. WO95/24391, WO 97/09040, WO 98/40353 and WO 98/50359.

A compound which effectively can be used for treatment or preventing of diabetes is (2R,3R,4R)-3,4-dihydroxy-2-hydroxymethylpyrrolidine.

Obesity or Appetite Regulation

Another field for the invention is obesity or appetite regulation.

Obesity is a well-known risk factor for the development of many very common diseases such as atherosclerosis, hypertension and diabetes. The incidence of obese people and thereby also these diseases is increasing throughout the entire industrialised world.

Due to its indirect but important effect as a risk factor in mortal and common diseases it will be important to find treatment for obesity or appetite regulation.

Exercise, diet modification and food restriction will reduce body weight but for most patients, this is not feasible. Pharmacological treatment available up to date only consists of Sibutramine (acting via serotonergic mechanisms, Knoll Pharm) and Orlistat (reducing fat uptake from the gut, Roche Pharm) neither reducing body weight effectively nor acceptably.

The term obesity implies an excess of adipose tissue. In this context obesity is best viewed as any degree of excess adiposity that imparts a health risk. The cut off between normal and obese individuals can only be approximated, but the health risk imparted by the obesity is probably a continuum with increasing adiposity. The Framingham study demonstrated that a 20% excess over desirable weight clearly imparted a health risk. (Mann GV N.Engl.J. Med 291:226, 1974). In the United States a National Institutes of Health consensus panel on obesity agreed that a 20% increase in relative weight or a body mass index (BMI=body weight in kilograms divided by the square of the height in meters) above the 85th percentile for young adults constitutes a health risk. By the use of these criteria 20 to 30 percent of adult men and 30 to 40 percent of adult women in the United States are obese. (NIH, Ann Intern Med 103:147, 1985).

Indeed, the prevalence of obesity has increased with 100% in most western countries the last 20 years, and this is very serious because even mild obesity increases the risk for pre-mature death, type 2 diabetes, coronary heart disease, hypertension, atherosclerosis, sleep apnea and respiratory problems, osteoarthritis, gallbladder disease and certain types of cancer (endometrial, breast, prostate and colon). Because of the high prevalence of obesity and its health consequences, its prevention and treatment should be a high public health priority.

When energy intake exceeds expenditure, the excess calories are stored in adipose tissue, and if this net positive balance is prolonged, obesity results, i.e. there are two components to weight balance, and an abnormality on either side (intake or expenditure) can lead to obesity.

The regulation of feeding behaviour is incompletely understood. Certain is that brain neurochemicals located in specific hypothalamic nuclei regulate onset and termination of feeding. Several regulatory processes may influence these hypothalamic centres: Metabolic signals such as postprandial increases in plasma glucose and insulin; meal-induced gastric distension is another possible inhibitory factor. Local control by brain neurochemicals and catecholamines/beta3-adrenoceptors (inhibits feeding and stimulates energy expenditure). Psychological, social, and genetic factors also influence food intake.

At present a variety of techniques are available to effect initial weight loss. Unfortunately, initial weight loss is not an optimal therapeutic goal. Rather, the problem is that most obese patient eventually regain their weight. An effective means to establish and/or sustain weight loss is the major challenge in the treatment of obesity today.

Thus there remains today a need in the art for compositions and methods that are useful for the treatment or prophylaxis of obesity or appetite regulation.

One object of the present invention is to provide compounds, which can effectively be used for the treatment or prophylaxis of obesity or appetite regulation.

A compound which effectively can be used for the treatment or prophylaxis of obesity or appetite regulation is (2R,3R,4R)-3,4-dihydroxy-2-hydroxymethylpyrrolidine.

(2R,3R,4R)-3,4-Dihydroxy-2-hydroxymethylpyrrolidine (2R,3R,4R)-3,4-Dihydroxy-2-hydroxymethylpyrrolidine is a base with a pKa 8.22. As the base is an oil ordinary tablet formulation cannot be applied. Therefore there is a need to find a crystalline salt with suitable solid-state characteristics like a high melting point and low hygroscopicity.

(2R,3R,4R)-3,4-Dihydroxy-2-hydroxymethylpyrrolidine, hydrochloride, was disclosed in example 2 of WO 97/09040. The compound was prepared according to the method described by Overkleeft et al., Tetrahedron 50 (1994), 4215–4224, which is incorporated herein by reference.

However, the hydrochloride salt has some pharmaceutically undesirable properties. The hydrochloride salt is highly hygroscopic at relative room humidities above 50% and has a melting point of 116 ° C., which is rather low. For the choice of tablet formulation process it would be a big advantage to have a salt with a higher melting point.

For commercial use it is important to have a physiologically acceptable salt with good stability, good solubility, non-hygroscopicity, good bioavailability, good handling properties, like high melting point and a reproducible crystalline form.

SUMMARY OF THE INVENTION

It has now been discovered that (2R,3R,4R)-3,4-dihydroxy-2-hydroxymethyl-pyrrolidine, D-tartrate surprisingly has the above described desired properties.

Within one aspect, the present invention provides (2R,3R,4R)-3,4-dihydroxy-2-hydroxymethyl-pyrrolidine, D-tartrate.

Within another aspect of the invention there is provided a salt for the use as a medicament.

Within another aspect of the invention there is provided a use of the salt for the preparation of a pharmaceutical composition for the treatment or preventing of diabetes.

Within another aspect of the invention there is provided a use of a salt for the preparation of a pharmaceutical composition for the treatment or prophylaxis of obesity or appetite regulation.

Within another aspect of the invention there is provided a pharmaceutical composition comprising (2R,3R,4R)-3,4-dihydroxy-2-hydroxy-methylpyrrolidine,D-tartrate optionally together with a pharmaceutically acceptable carrier or diluent.

Within another aspect of the invention there is provided a process for the preparation of (2R, 3R,4R)-3,4-dihydroxy-2-hydroxymethyl-pyrrolidine, D-tartrate which process comprises dissolving D-tartaric acid and (2R,3R,4R)-3,4-dihydroxy-2-hydroxymethyl-pyrrolidine in a suitable solvent, and crystallizing the resulting salt from the solution.

Within another aspect of the invention there is provided a process for the preparation of (2R,3R,4R)-3,4-dihydroxy-2-hydroxymethyl-pyrrolidine, D-tartrate which process comprises dissolving D-tartaric acid and a salt of (2R,3R,4R)-3,4-dihydroxy-2-hydroxymethylpyrrolidine in a suitable solvent, and crystallizing the resulting salt from the solution.

Furthermore a process for the preparation of (2R,3R,4R)-3,4-dihydroxy-2-hydroxymethyl-pyrrolidine, D-tartrate is produced by reducing 2,3,5-Tri-O-benzyl-1,4-dideoxy-1,4-imino-D-arabinitol with Pd/C in glacial acetic acid. The formed, oily (2R,3R,4R)-3,4-dihydroxy-2-hydroxymethyl-pyrrolidine,acetate is dissolved in methanol and added to a solution containing D-tartaric acid at reflux and (2R,3R,4R)-3,4-dihydroxy-2-hydroxymethylpyrrolidine, D-tartrate is formed and can be isolated by filtration. Ion exchange chromatography is thereby avoided.

Within another aspect of the invention there is provided a method of using the salt according to the invention for the treatment or preventing of diabetes and a method of using the salt according to the invention for the treatment or prophylaxis of obesity or appetite regulation.

DETAILED DESCRIPTION OF THE INVENTION

The present invention relates to the D-tartrate salt of (2R,3R,4R)-3,4-dihydroxy-2-hydroxymethylpyrrolidine having the structural formula I as shown herein below.

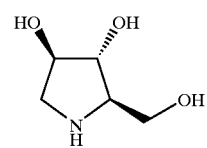

Formula I

Hereinafter the above compound of formula I is referred to as compound I.

A salt of compound I is provided in the form of crystals, which have good stability characteristics in e.g. non-hygroscopicity, good solubility in e.g. water, good bioavailability, good handling properties in e.g. high melting point, and a reproducible crystalline form.

The present invention also provides a process for the preparation of a salt of compound I, which process comprises dissolving compound I in a suitable solvent, and dissolving a specific acid, in the same kind of solvent, and adding the solution of the acid to the solution of compound I, and crystallizing the resulting salt from the solution. Examples of the common solvents include but are not limited to organic solvents in particular lower aliphatic alcohol's such as methanol, ethanol, 2-propanol, 2-butanol, 1-hexanol and solvents like acetone, isobutylmethylketone and tetrahydrofuran. Preferred solvents are methanol, ethanol, 2-propanol and acetone. The mixture of the components is conveniently performed at temperatures from 40° C. to reflux before cooling down to 0–5° C. and collection of the crystals by filtration. The speed of cooling down, the crystallisation temperature and the solvent may have influence on the crystalline form obtained. Optionally, seeding crystals are added if precipitation has not occurred within 1–2 hours after mixing.

The present invention also provides a pharmaceutical composition comprising a salt of compound I optionally together with a pharmaceutically acceptable carrier or diluent.

A salt of compound I may be used in human and veterinary medicine for the treatment or preventing of diabetes and for the treatment or prophylaxis of obesity or appetite regulation.

A salt of compound I may be used in human and veterinary medicine for the treatment or preventing of diabetes, and especially non-insulin dependent diabetes (NIDDM or type 2 diabetes) including overnight or meal treatment.

A still further objection of this invention is to provide a salt of compound I which can effectively be used as an inhibitor of glucose production from the liver.

A still further objection of this invention is to provide a salt of compound I which can effectively be used as glycogen phosphorylase inhibitor.

For use within the present invention (2R,3R,4R)-3,4-dihydroxy-2-hydroxymethyl-pyrrolidine,D-tartrate may be formulated with a pharmaceutically acceptable carrier or excipient to provide a medicament for parenteral, oral, nasal, rectal, pulmonal, buccal, subdermal or intradermal or transdermal administration according to conventional methods. Formulations may further include one or more diluents, fillers, emulsifiers, preservatives, buffers, excipients, etc. and may be provided in such forms as liquids, powders, emulsions, suppositories, liposomes, transdermal patches, controlled release, dermal implants, tablets, etc.

One skilled in this art may formulate the compound in an appropriate manner, and in accordance with accepted practices, such as those disclosed in *Remington's Pharmaceutical Sciences,* 1985 or *Remington's Pharmaceutical Sciences,* Gennaro, ed., Mack Publishing Co., Easton, Pa., 1990, or *Remington: The Science and Practice of Pharmacy,* 19th Edition (1995), which are incorporated by reference. The compositions may appear in conventional forms, for example capsules, tablets, aerosols, solutions, suspensions or topical applications.

The pharmaceutical carrier or diluent employed may be a conventional solid or liquid carrier. Examples of solid carriers are lactose, terra alba, sucrose, cyclodextrin, talc, gelatin, agar, pectin, acacia, magnesium stearate, stearic acid or lower alkyl ethers of cellulose. Examples of liquid carriers are syrup, peanut oil, olive oil, phospholipids, fatty acids, fatty acid amines, polyoxyethylene or water.

Similarly, the carrier or diluent may include any sustained release material known in the art, such as glyceryl monostearate or glyceryl distearate, alone or mixed with a wax.

The compositions of this invention are usually adapted for oral administration.

For oral administration (2R,3R,4R)-3,4-dihydroxy-2-hydroxymethylpyrrolidine,D-tartrate is prepared in a suitable form, such as a tablet or capsule. Typically, the salt of compound I is combined with a carrier and molded into a tablet. Suitable carriers in this regard include starch, sugars, dicalcium phosphate, calcium stearate, magnesium stearate and the like. Such compositions may further include one or more auxiliary substances, such as wetting agents, emulsifiers, preservatives, stabilizers, colouring additives, etc.

Pharmaceutical compositions are administered one or more times per day or week. An effective amount of such a pharmaceutical composition is the amount that provides a clinically significant effect. Such amounts will depend, in part, on the particular condition to be treated, age, weight, and general health of the patient, and other factors evident to those skilled in the art.

The pharmaceutical compositions may be administered in unit dosage form one or more times per day or week. In the alternative, they may be provided as controlled release formulations suitable for dermal implantation. Implants are formulated to provide release of active compound over the desired period of time, which can be up to several years. Controlled-release formulations are disclosed by, for example, Sanders et al., *J Pharm Sci* 73 (1964), 1294–1297, 1984; U.S. Pat. No. 4,489,056; and U.S. Pat. No. 4,210,644, which are incorporated herein by reference.

The composition is usually presented as a unit dose composition containing 0.1–1000 mg of a salt of compound I in accordance with the invention for oral dosing. Typical dosage for diabetes effect would vary between 0.1–750 mg, preferably between 1–500 mg per day either once or divided in 2 or 3 doses when administered orally or 2 or 3 times per week or once weekly or once per 14 days.

Preferred unit dosage forms include in solid form, tablets or capsules, in liquid form, solutions, suspensions, emulsions, elixirs or capsules filled with the same, or in form of sterile injectable solutions, or patches, vagitories, vaginal rings or long lasting implantates.

The composition of this invention may be formulated by conventional methods of galenic pharmacy.

Conventional excipients are such pharmaceutically acceptable organic or inorganic carrier substances suitable for parenteral or oral application which do not deleteriously react with the active compound I.

Examples of such carriers are water, salt solutions, alcohols, polyethylene glycols, polyhydroxyethoxylated castor oil, syrup, peanut oil, olive oil, gelatin, lactose, terra alba, sucrose, agar, pectin, acacia, amylose, magnesium stearate, talc, silicic acid, stearic acid, fatty acid monoglycerides and diglycerides, pentaerythritol fatty acid esters, hydroxymethylcellulose and polyvinylpyrrolidone and calcium phosphates.

The pharmaceutical preparations can be sterilized and mixed, if desired, with auxiliary agents, such as binders, lubricants, preservatives, disintegrants, stabilizers, wetting agents, emulsifiers, salt for influencing osmotic pressure, buffers and/or colouring substances and the like, which do not deleteriously react with the active compound.

Particularly suitable for parenteral application are injectable solutions or suspensions, preferably aqueous solutions with the active compound dissolved in polyhydroxylated castor oil.

Particularly suitable for oral administration are tablets, dragees, or capsules having talc and/or a carbohydrate carrier or binder or the like, the carrier preferably being lactose or calcium phosphate and/or corn starch and/or potato starch. A syrup, elixir or like can be used when a sweetened vehicle can be employed.

A typical tablet, which may be prepared by conventional tabletting techniques, contains: 50 mg of compound I in form of the salt, 100 mg of lactose, 30 mg of corn starch, 3 mg of talc powder, 3 mg of colloidal silicon dioxide and 2 mg of magnesium stearate.

The present invention is further illustrated by the following examples, which, however, are not to be construed as limiting the scope of protection. The features disclosed in the foregoing description and in the following examples may, both separately and in any combination thereof, be material for realising the invention in diverse forms thereof.

(2R,3R,4R)-3,4-Dihydroxy-2-hydroxymethylpyrrolidine, D-tartrate is synthesized, purified and crystallized as described in the following examples.

EXAMPLES

Compound I, (2R,3R,4R)-3,4-dihydroxy-2-hydroxymethylpyrrolidine, has the structural formula I as shown herein below.

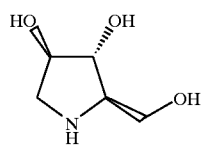

Formula I

Example 1

The hydrochloride salt of compound I is disclosed in example 2 of WO 97/09040. The hydrochloride salt of compound I may be prepared as described by Overkleeft et al., Tetrahedron 50 (1994), 4215–4224, which is incorporated herein by reference.

In Brief, the Hydrochloride Salt of Compound I can be Prepared as Follows 2,3,5-Tri-O-benzyl-D-arabinofuranose is oxidised via DMSO/acetic acid anhydride to its lactone. 2,3,5-Tri-O-benzyl-D-arabino-1,4-lactone was reacted with ammonia to furnish the arabinoamide which then is oxidised via Dess Martin agent to the 4-oxo-arabinoamide. Treatment with ammonia and affords a 1:1 C4 isomeric mixture of the hydroxylactams. The isomeric mixture is reduced with sodium cyanoborohydride to afford pure 2,3,5-Tri-O-benzyl-D-arabino-1,4-lactam after purification. The lactame is reduced to 2,3,5-Tri-O-benzyl-1,4-dideoxy-1,4-imino-D-arabinitol with LiAIH$_4$. Subsequent reduction with Pd/C containing HCl followed by purification and crystallisation led to pure (2R,3R,4R)-3,4-dihydroxy-2-hydroxymethylpyrrolidine, HCl.

(2R,3R,4R)-3,4-dihydroxy-2-hydroxymethylpyrrolidine.

A normal glass column for flash chromatography (diameter 2 cm) was filled with ion exchange resin from Rohm & Haas Ambersep 900 OH to a height of 10.4 cm. 50 ml water was added. The column was rinsed with 50 ml water and then with 150 ml 1M NaOH over a period of 30 min. then, the column was washed with 3×50 ml water and 3×50 ml methanol. 2.00 g compound I, HCl was dissolved in 20 ml methanol and run through the column 5 times over a total period of 10 min. The final methanolic solution was collected and the solvent removed. The residual brownish oil was stripped with ethanol to removed small amounts of water. The final yield of compound I free base was 1.66 g (93%) and contained less than 0.1% ionogen chlorine measured by elemental analysis.

(2R,4R)-3,4-Dihydroxy-2-hydroxymethylpyrrolidine, D-tartrate.

A solution of D-tartaric acid (225 mg, 1.5 mmol) in methanol (1 ml) is added to a solution of compound I (200 mg, 1.5 mmol) in methanol (4 ml). The mixture is cooled at −18° C. for 2 hours. The formed precipitate is collected, washed with cold methanol (1 ml) and dried to give white crystals of (2R,3R,4R)-3,4-dihydroxy-2-hydroxy methyl-pyrrolidine, D-tartrate (Yield: 250 mg) (C$_5$H$_{11}$NO$_3$·C$_4$H$_6$O$_6$; MW: 283,24g/mol). Melting point of 148° C.

An evaluation of the hygroscopicity was carried out by exposing the salt to increasing humidity and measuring the mass increase in a Dynamic Vapour Sorption Instrument (DVS). The critical relative humidity value is found to be above 80%.

Example 2

A more direct way to synthesise 3,4-dihydroxy-2-hydroxymethylpyrrolidine, D-tartrate is by reducing 2,3,5-Tri-O-benzyl-1,4-dideoxy-1,4-imino-D-arabinitol with Pd/C in glacial acetic acid. The formed, oily (2R,3R,4R)-3,4-dihydroxy-2-hydroxymethyl-pyrrolidine,acetate is dissolved in methanol and added to a solution containing D-tartraric acid at reflux and (2R,3R,4R)-3,4-dihydroxy-2-hydroxymethylpyrrolidine, D-tartrate is formed and can be isolated by filtration. Ion exchange chromatography is thereby avoided.

Synthesis of (2R,3R,4R)-3,4-dihydroxy-2-hydroxymethylpyrrolidine, D-tartrate via (2R,3R,4R)-3,4-dihydroxy-2-hydroxymethylpyrrolidine, acetate 10 g(25 mmol) of 2,3,5-Tri-O-benzyl-1,4-dideoxy-1,4-imino-D-arabinitol is dissolved in 40 ml glacial acetic acid. Heat is developed and the solution gets dark. 1.2 g of 10% Pd/C (50% wet) is added and stirred overnight at 20–25° C. under nitrogen atmosphere. The catalyst is removed by filtration and washed with 10 ml of glacial acetic acid. Another 1.2g of 10% Pd/C (50% wet) is added and the mixture is left under hydrogen atmosphere at 3bar and 50° C. Full conversion is obtained after 4½h. The mixture is cooled to 20–25° C. and filtered. The filtrate is evaporated and stripped 3 times with 20 ml of a 50:50 methanol/toluene mixture to remove excess acetic acid leaving 7.0 g (>100%) of an oily, dark residue with an extensive odour of acetic acid.

The oily residue is dissolved in 15 ml methanol and slowly added to 15ml refluxing methanol containing 4.4 g (29 mmol) D-tartaric acid. When around one third of the mixture is added (2R,3R,4R)-3,4-dihydroxy-2-hydroxymethylpyrrolidine,D-tartrate begins to crystallise out of the solution. The temperature is kept at reflux for additional ½h after all (2R,3R,4R)-3,4-dihydroxy-2-hydroxymethylpyrrolidine,acetate is added and then cooled to 20–25° C. by standing overnight. The next day the slurry is filtered and the filter cake dried to constant weight leaving 6.1 g (86%) of (2R,3R,4R)-3,4-dihydroxy-2-hydroxymethylpyrrolidine, D-tartrate (C$_5$H$_{11}$NO$_3$·C$_4$H$_6$O$_6$; MW: 283,24 g/mol) as off white crystals. Melting point of 147° C.

What is claimed is:

1. A composition comprising (2R,3R,4R)-3,4-dihydroxy-2-hydroxymethylpyrrolidine, D-tartrate.

2. A process for the preparation of (2R,3R,4R)-3,4-dihydroxy-2-hydroxymethyl-pyrrolidine, D-tartrate, comprising dissolving D-tartaric acid and (2R,3R,4R)-3,4-dihydroxy-2-hydroxymethylpyrrolidine in a solvent, and crystallizing the resulting salt from the solvent.

3. A process for the preparation of (2R,3R,4R)-3,4-dihydroxy-2-hydroxymethyl-pyrrolidine, D-tartrate, comprising dissolving D-tartaric acid and a salt of (2R,3R,4R)-3,4-dihydroxy-2-hydroxymethylpyrrolidine in a solvent, and crystallizing (2R,3R,4R)-3,4-dihydroxy-2-hydroxymethyl-pyrrolidine, D-tartrate from the solvent.

4. The process of claim 3, wherein the salt of (2R,3R,4R)-3,4-dihydroxy-2-hydroxymethylpyrrolidine is acetate.

5. The process of claim 2, wherein the solvent is methanol.

6. A pharmaceutical composition comprising the compound of claim 1, and optionally a pharmaceutically acceptable carrier or diluent.

7. The pharmaceutical composition of claim 6 in the form of a dosage unit containing about 0.1–1000 mg (2R,3R,4R)-3,4-dihydroxy-2-hydroxymethylpyrrolidine, D-tartrate.

8. A method for the treatment of diabetes comprising administering to a patient an effective amount of the compound of claim 1.

9. A method for the treatment or prophylaxis of obesity or appetite regulation comprising administering to a patient an effective amount of the compound of claim 1.

* * * * *